United States Patent
Landon

(10) Patent No.: US 10,980,915 B2
(45) Date of Patent: Apr. 20, 2021

(54) PATELLAR IMPLANTS

(71) Applicant: Smith & Nephew, Inc., Memphis, TN (US)

(72) Inventor: Ryan Lloyd Landon, Southaven, MS (US)

(73) Assignee: Smith & Nephew, Inc., Memphis, TN (US)

( * ) Notice: Subject to any disclaimer, the term of this patent is extended or adjusted under 35 U.S.C. 154(b) by 47 days.

(21) Appl. No.: 15/799,093

(22) Filed: Oct. 31, 2017

(65) Prior Publication Data

US 2018/0064845 A1 Mar. 8, 2018

Related U.S. Application Data

(63) Continuation of application No. 13/816,852, filed as application No. PCT/US2011/047597 on Aug. 12, 2011, now Pat. No. 9,801,974.

(60) Provisional application No. 61/373,585, filed on Aug. 13, 2010.

(51) Int. Cl.
| | |
|---|---|
| *A61F 2/64* | (2006.01) |
| *A61L 27/16* | (2006.01) |
| *A61F 2/38* | (2006.01) |
| *B33Y 80/00* | (2015.01) |
| *A61F 2/30* | (2006.01) |

(52) U.S. Cl.
CPC ............ *A61L 27/16* (2013.01); *A61F 2/3877* (2013.01); *A61F 2/3094* (2013.01); *A61F 2002/3092* (2013.01); *A61F 2002/30892* (2013.01); *A61F 2002/30968* (2013.01); *A61F 2310/00017* (2013.01); *A61F 2310/00023* (2013.01); *A61F 2310/00029* (2013.01); *A61F 2310/00089* (2013.01); *A61F 2310/00179* (2013.01); *B33Y 80/00* (2014.12)

(58) Field of Classification Search
CPC .............. A61F 2/3877; A61F 2002/648; A61F 2300/0065
See application file for complete search history.

(56) References Cited

U.S. PATENT DOCUMENTS

| | | | |
|---|---|---|---|
| 4,944,756 A | 7/1990 | Kenna | |
| 5,024,670 A * | 6/1991 | Smith | A61F 2/3877 128/898 |
| 6,132,470 A | 10/2000 | Berman | |
| 6,855,150 B1 | 2/2005 | Linehan | |
| 2003/0083751 A1 | 5/2003 | Tornier | |
| 2004/0143336 A1 | 7/2004 | Burkinshaw | |

(Continued)

FOREIGN PATENT DOCUMENTS

WO 2004110319 A1 12/2004

OTHER PUBLICATIONS

International Search Report; International Searching Authority; International Application No. PCT/US2011/047597; dated Mar. 22, 2012; Smith & Nephew, Inc.

*Primary Examiner* — Dinah Baria
(74) *Attorney, Agent, or Firm* — Kacvinsky Daisak Bluni PLLC

(57) ABSTRACT

A patellar implant including a base portion formed of a porous metallic material, a polymeric portion formed of a polymeric material and attached to the base portion, and a membrane embedded between the base portion and the polymeric portion to provide a barrier between the porous metallic material and the polymer material.

20 Claims, 4 Drawing Sheets

(56) References Cited

U.S. PATENT DOCUMENTS

| | | |
|---|---|---|
| 2004/0254645 A1 | 12/2004 | Arnin et al. |
| 2007/0255412 A1* | 11/2007 | Hajaj ................. A61F 2/38 623/17.11 |
| 2007/0265708 A1 | 11/2007 | Brown et al. |
| 2010/0204801 A1 | 8/2010 | Walker et al. |
| 2010/0256758 A1 | 10/2010 | Gordon et al. |

* cited by examiner

PATELLAR IMPLANTS

CROSS REFERENCE TO RELATED APPLICATIONS

The present application is a continuation of U.S. application Ser. No. 13/816,852 filed on Feb. 13, 2013 and issued as U.S. Pat. No. 9,801,974, which is a U.S. National Phase of International PCT Application No. PCT/US2011/047597 filed on Aug. 12, 2011, which claims the benefit of U.S. Provisional Patent Application Ser. No. 61/373,585 filed on Aug. 13, 2010, the contents of each application hereby incorporated by reference in its entirety.

FIELD OF THE INVENTION

The present invention relates generally to patellar implants that are designed to form a patellar portion (or knee cap) that replaces a part of a natural knee cap, and particularly to patellar implants that are designed to cooperate and articulate against a femoral component of a total or partial knee prosthesis.

BACKGROUND OF THE INVENTION

Joint replacement, and particularly knee replacement, has become increasingly widespread. Various knee prostheses and procedures have been developed to treat the debilitating effects of knee joint deterioration (e.g., such as that caused by arthritis, injury, or disease). A fairly common procedure used to repair a patient's knee is a total knee replacement, in which the tibia is resected and replaced with a tibial component, and the femur is resected and replaced with a femoral component. In some instances, the surgeon will also replace the articulating surface on the posterior aspect of the patella where it interfaces with the femoral component, which can help improve the results of the total knee replacements. A surgeon may also elect to perform a partial knee replacement where only some portions of the patient's knee will be replaced. It may also be desirable for the surgeon to replace the articulating surface of the patella in a partial knee replacement.

SUMMARY OF THE INVENTION

The various embodiments of the present invention described below and shown in the Figures provide patellar implants that are optimally shaped and designed to provide a two part implant having a strong base (metal or other significantly strong material) with a molded outer material (polymer or other softer, smoother material) at least on one side, to provide a smooth friction surface to contact the femoral portion of a patient's knee.

Further areas of applicability of the invention will become apparent from the detailed description provided hereinafter. It should be understood that the detailed description and specific examples, while indicating the particular embodiment of the invention, are intended for purposes of illustration only and are not intended to limit the scope of the invention.

DETAILED DESCRIPTION OF THE EMBODIMENTS

Figure 1:
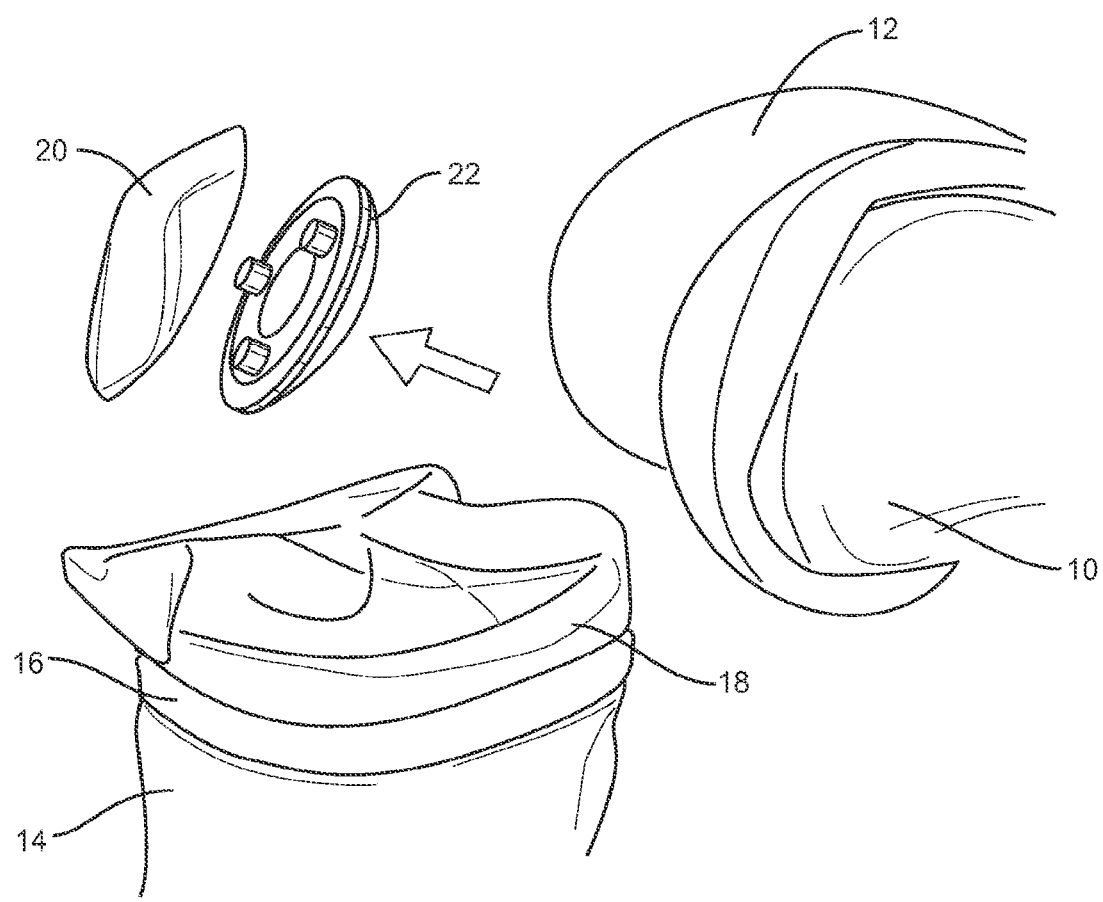
FIG. 1 shows a side perspective view of how a patellar implant may be secured to a portion of a natural patella.
Figure 2:
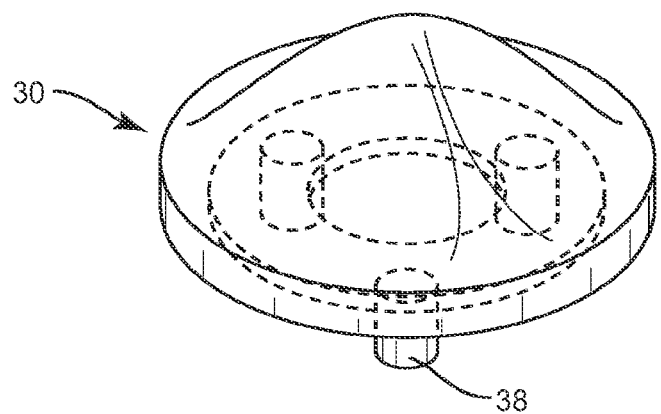
FIG. 2 shows a top perspective view of a patellar implant according to one embodiment of the invention.
Figure 3:
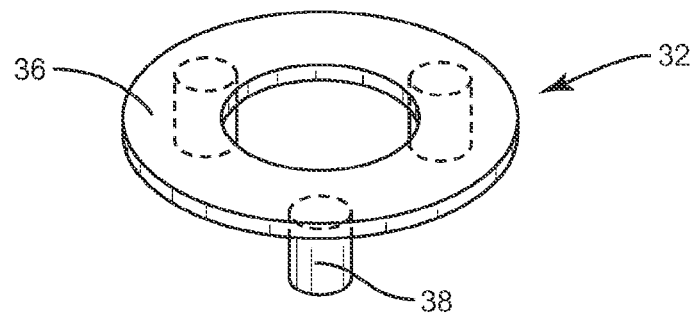
FIG. 3 shows a top perspective view of the base portion of the patellar implant.
Figure 4:
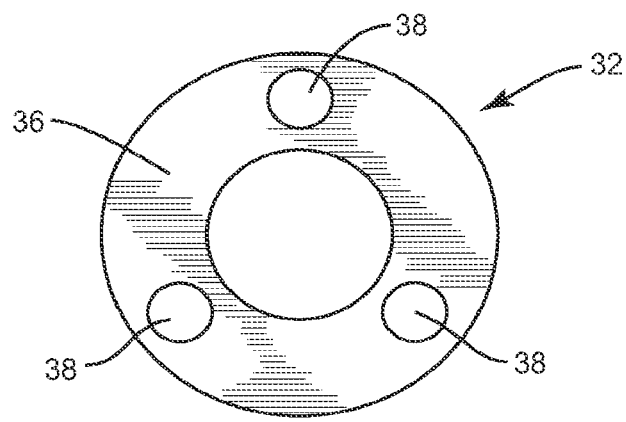
FIG. 4 shows a bottom plan view of the base portion of the patellar implant.

For the purpose of promoting an understanding of the principles of the present invention, reference will now be made to embodiments illustrated in the drawings and specific language will be used to describe the same. It will nevertheless be understood that no limitation of the scope of the invention is being intended. Any alternatives and further modifications in the described embodiments, and any further applications of the principles of the invention as described herein are contemplated as would normally occur to one skilled in the art to which the invention relates.

Embodiments of the present invention provide patellar prostheses that are designed to form a patella portion or knee cap that replaces a part of a natural knee cap. FIG. 1 shows the state of the art on how a patellar implant would typically be secured to a portion of a natural patella. The patient's natural knee bone is shown; the femoral bone portion 10 with a femoral knee implant 12 shown attached to the femur; a tibial bone portion 14 with a tibial tray implant 16 and spacer 18 is shown attached to the tibia; and a patellar bone portion 20 is shown having a patellar implant 22 being attached to the patellar bone portion 20. It is common practice to not remove the whole patellar bone, or knee cap when doing a knee implant. It is always desirable to leave as much natural bone as possible. So typically, a patellar implant will only be affixed to the inside portion of the patellar bone portion to provide a smooth surface which will then interact with the femoral knee implant 12.

Figure 5:
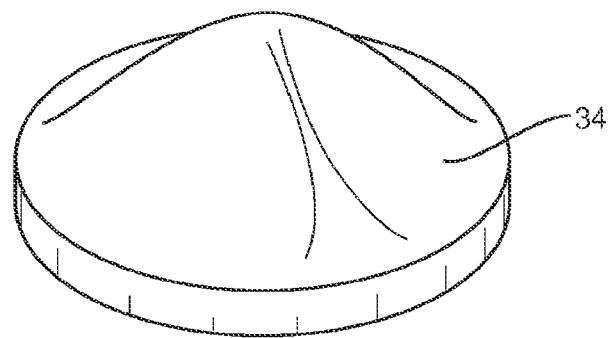
FIG. 5 shows a top perspective view of the molded or snap fit polymer portion of the patellar implant.
Figure 6:
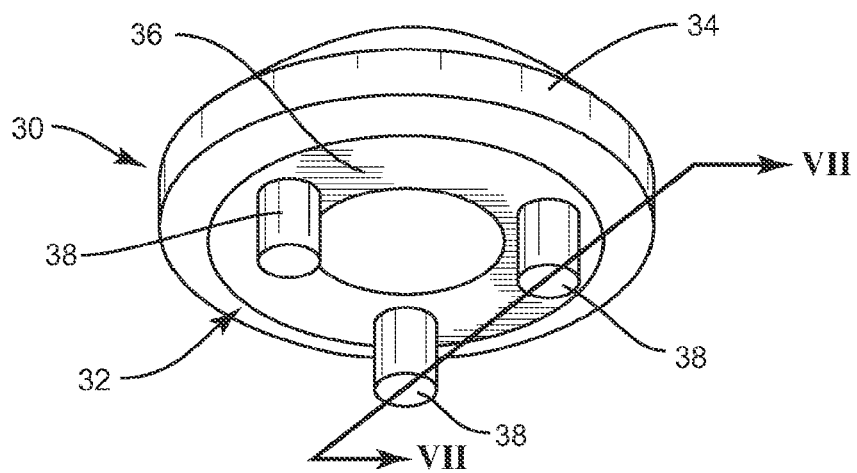
FIG. 6 shows a bottom perspective view of the patellar implant with the base portion and polymer portion connected together to form the patellar implant.
Figure 7:
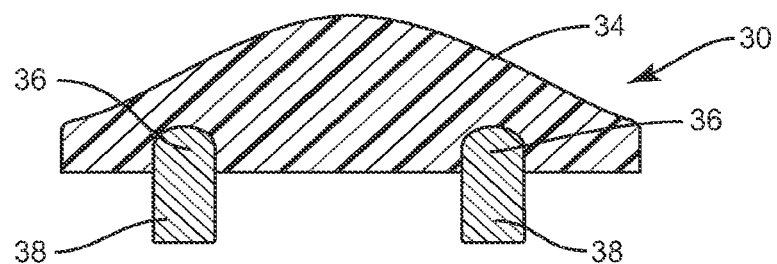
FIG. 7 shows a side cross-sectional view of the patellar implant taken along line 7-7 shown in FIG. 6.

In a first embodiment, shown in FIGS. 2-7, a patellar implant 30 is shown having a base portion 32 made of a metal (i.e., titanium, titanium alloy, zirconium, chrome cobalt, stainless steel or other medical grade material, such as a ceramic) having an appropriate rigidity to prevent bending when positioned within a patient's body and a polymeric portion 34 made of an appropriate polymeric material which is molded or snap fit onto the base portion of the patellar implant 30. The polymeric portion 34 may be made of a polyethylene or a cross-linked polyethylene. References to FIGS. 3 and 4, the base portion 32 has a circular ring 36 with depending pegs 38 having a porous coating or surface treatment. The porous coating or surface treatment allows for the ingrowth of the patient's natural bone growth when the patellar implant is implanted into a portion of the patient's natural patella 20. It is also possible that the entire base portion 32 be manufactured out of a porous material to allow for both the polymeric portion to be molded to such porous surface as well as to allow boney tissue ingrowth to those areas not covered by the polymeric portion. Reference to FIGS. 5 and 6, the polymeric portion 34 is shown either molded or snap fit onto the base portion 32 to form a patellar implant 30. The polymeric portion 34 may be overmolded, compression molded, injection molded, or cold molded (or any other molding process may be used) over the base portion to complete the patellar implant 30. In use, the pegs 38 of the patellar implant 30 may be press fit, glued with bone cement or otherwise adhered into the remaining natural portion of the patella 20. FIG. 7 shows a cross sectional view of the patellar implant 30 with the polymeric portion 34 molded or snap fit about the ring 36.

In the embodiment shown in FIGS. 2-7, the base portion 32 is shown with three depending pegs 38. However, it may also be desirable to have any number of pegs and the pegs can be of various shapes including various cruciform shapes. It may be desirable to have a single peg that has a plurality of spokes (not shown) extending from a portion of such pegs back to the annular ring portion 36. The ring portion 32 may also have various cutouts or notches provided about its periphery. The ring portion 32 could also be a discontinuous ring depending on the overall thickness and diameter of the ring portion 32.

Figure 9:
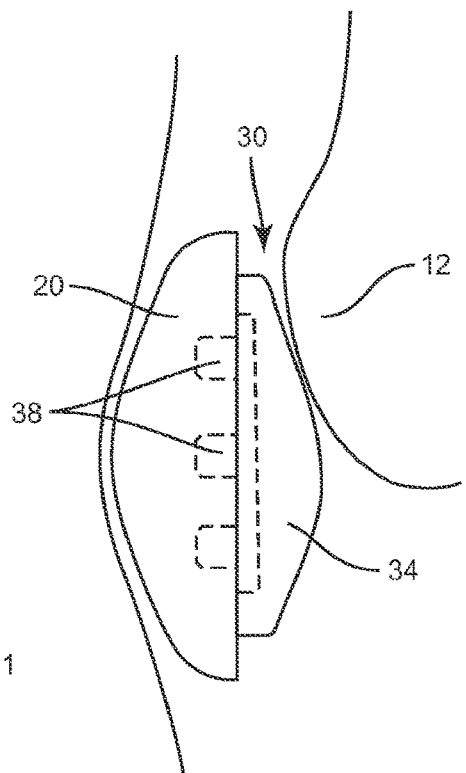
FIG. 9 shows a side view of the patellar implant of the present invention in position under the skin and adjacent a patient's femoral bone portion.

FIG. 9 shows the patellar implant 30 of the present inventions shown connected to the remaining natural portion of a patient's patella and in position adjacent the patient's femoral knee implants 12. As can be seen in FIGS. 1 and 9, the femoral bone portion 12 moves continuously with respect to the patient's patellar implant 30 in the course of normal leg movement. It is therefore desirable that the patellar implant 30 allow the femoral knee implant 12 and bone portion 10 to move freely and smoothly throughout the full range of motion by a patient during normal daily activities.

Figure 8:
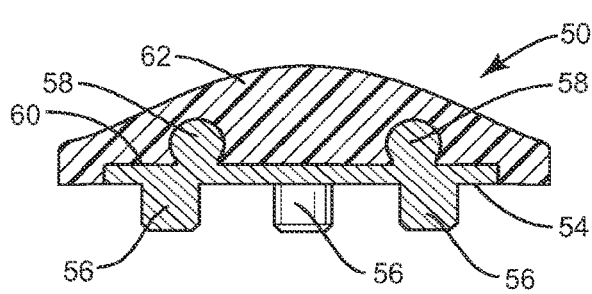
FIG. 8 shows a side cross-sectional view of an alternate embodiment of the patellar implant of the present invention.

In an alternate embodiment, FIG. 8 shows a patellar implant 50 having a base portion 52 with a central flat ring portion 54 with depending pegs 56 and an annular ring portion 58 positioned on the upper surface 60 of the flat ring portion 54. The base portion 52 can be made of a metal or stiff portion having a porous coating or surface treatment. The base portion 52 can also be made of a porous material throughout as long as such material is strong enough to prevent bending of the patellar implant 50 when the patellar implant 30 is positioned within the patient's knee construct. The polymeric portion 62 of the patellar implant 50 is then molded or snap fit over the body of the base portion 52 covering the flat ring portion 54 and annular ring portion 58. The annular ring 58 imparts a significant strength component to the overall implant 50 allowing the base component 52 to be as thin as possible to allow for a maximum thickness of the polymeric portion 62. The rounded edges of the annular ring portion 58 and central flat ring 54 assist in minimizing stress concentrations to resist any metal/polymeric material de-bonding or separation.

Figure 10:
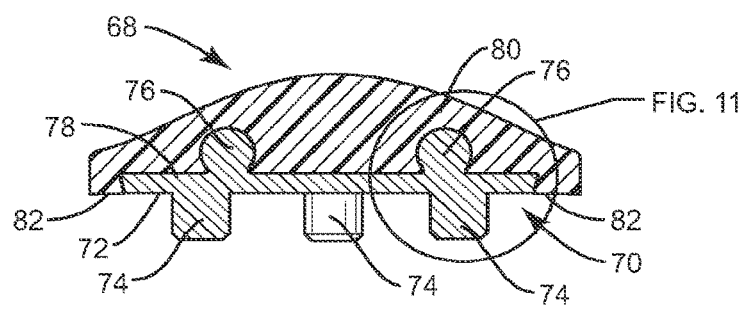
FIG. 10 shows a side cross-sectional view of an alternate embodiment of the patellar implant of the present invention.
Figure 11:
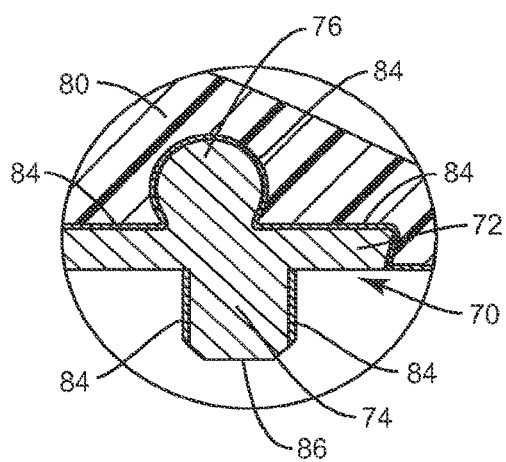
FIG. 11 shows an enlarged view of a portion of the patellar implant shown in FIG. 10.

FIG. 10 shows yet another embodiment of the present invention wherein the base portion 70 of the patellar implant 68 is manufactured out of a porous metal material having a flat circular base portion 72 with depending pegs 74 therefrom. An annular ring 76 is machined or attached to the upper surface 78 of the flat circular base portion 72 such that no sharp edges are provided about the base portion 72. The polymeric portion 80 is molded about the base portion 72 such that the annular ring 76 is encapsulated and the polymeric material 80 extends around the sides 82 of the flat circular base 72 to provide a dovetail lock about the sides of the patellar implant 68. FIG. 11 shows an enlarged portion of the base portion 72 and polymeric material 80 connection about the annular ring 76 and flat circular base portion 72. The base portion 72 is shown with a thin impermeable membrane 84 about portions of the base portion 72 to prevent the flow of backside wear particles. Backside wear particles are created when a metal component rubs or wears against a polymeric material. The wear particles are irritants within the body which can cause infection or other medical issues within the body. The membrane 84 could also be provided slightly below the surface of the base portion 72 to allow the polymeric material to bond with the porous surface of the base member while still encapsulating any wear particles between the embedded membrane and the polymeric portion of the patellar implant. A depending peg 74 is also shown in FIG. 11 illustrating how the thin membrane 84 could be applied to portions of the peg 74 to prevent or limit ingrowth of boney tissue along the sides of the pegs and yet allow for boney ingrowth at the bottom portions 86 of the pegs 74. This would allow for the tissue ingrowth to assist in capturing the patellar implant 68 within the remaining natural patella (20 in FIG. 1) while allowing for easier removal of the patellar implant in a revision situation.

Figure 12:
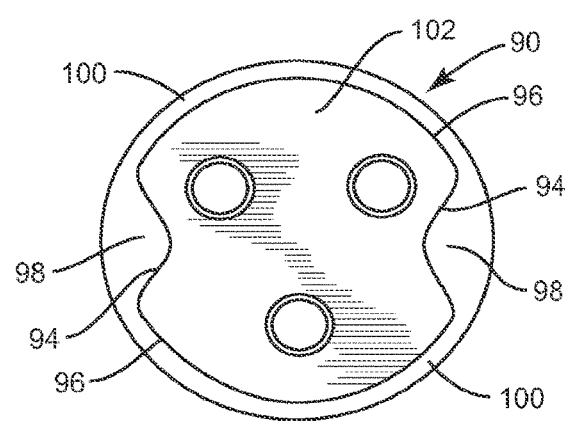
FIG. 12 shows a bottom view of yet another alternate embodiment of the patellar implant of the present invention.

FIG. 12 shows yet another embodiment of the present invention showing a patellar implant 90 having a flat circular base portion 92 having a pair of indentations provided about the periphery 96 of the base portion 92 provided at approximately 180 degrees apart. The polymeric material 94 may fill in this area 98 of the indentations and a polymeric rim 100 may be provided about the periphery of the circular base portion 92. The indentations 94 would be positioned on the superior and inferior poles of the implant when positioned with respect to the patient's natural knee cap (20 in FIG. 1) and the femoral components (12 in FIG. 1). The indentations 94 of the patellar implant 90 allow for flexation of the patient's knee cap without creating undue stress risers of the flat metal circular base portion 92. The bottom surface 102 of the base portion 92 would be provided with a boney tissue in-growth surface or be manufactured out of a metal material with boney in-growth properties.

It may be desirable to position the indentations 94 on medial to lateral poles of the implant when positioned with respect to a patient's natural knee cap. When the indentations are positioned in this fashion a greater volume of polymeric material would be existing at the sides of the patellar implant where the patellar implant would rub up against the femoral components of the artificial knee construct.

It may also be desirable to provide a patellar implant having a base portion and polymeric portion wherein the overall shape of the base portion can be modified intraoperatively such that the base portion could then be affixed to the polymeric portion of the implant. It may be necessary to cut away the pegs from the base portion such as during revision surgery.

Furthermore, the embodiments discussed above have all included a strong base portion with a softer polymeric portion for interacting with the other anatomy of the patient such as the femoral component. However, it may be desirable that the softer portion be made of a zirconium or other non-plastic material in case it is desirable to provide a hard-on-hard (or metal-on-metal) surface.

In some embodiments, the base portion may be manufactured using Selective Laser Sintered technologies ("SLS") or other free-form fabrication technologies, such as one or more of the EOS Laser-Sintering systems available from EOS GmbH of Munich, Germany. For instance, in some embodiments, the entire base portion may be formed as a monolithic base portion (including any porous or other in-growth promoting surfaces or materials). In other embodiments, portions of the base portion may be formed using SLS technology and then additional in-growth materials or surfaces could be added or applied to the implant. In other embodiments, portions or the entire base portion can be formed using casting or other technologies or methods. In some embodiments, a non-porous base portion may be formed using SLS technologies and subsequently that base portion may be subjected to acid etching, grit blasting, plasma spraying (e.g. of titanium oxide or another metal to promote in-growth of tissue) or other treatments.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the invention should not be limited by any of the above-described exemplary embodiments, but should be defined only in accordance with the claims and their equivalents.

What is claimed is:

1. A patellar implant, comprising:
a base portion comprising a flat circular shape with a top surface and a bottom surface, the top surface comprising an annular ring extending therefrom, the bottom surface having a plurality of attachment pegs extending therefrom, wherein the top surface and the bottom surface include a porous metallic material, and the annular ring comprises a toroidal shape with inner and outer surfaces and a portion of the inner surface overhangs an inner portion of the top surface and a portion of the outer surface overhangs an outer portion of the top surface; and
a polymeric portion comprising a polymeric material, the polymeric portion attached to the top surface of the base portion about at least part of the inner and outer surfaces of the annular ring and such that the polymeric material bonds with the porous metallic material included in the top surface of the base portion, wherein the polymeric portion attached to the base portion fills at least a portion of the overhang between the portion of the inner surface of the toroidal shape and the inner portion of the top surface of the base portion and the polymeric portion attached to the base portion fills at least a portion of the overhang between the portion of the outer surface of the toroidal shape and the outer portion of the top surface of the base portion.

2. The implant of claim 1, comprising a membrane embedded below the top surface of the base portion.

3. The implant of claim 2, wherein the membrane is embedded in the porous metallic material of the base portion.

4. The implant of claim 2, wherein the embedded membrane is positioned in contact with both the porous top surface of the base portion and the polymer material of the polymeric portion.

5. The implant of claim 1, wherein at least one of the plurality of attachment pegs is formed of the porous metallic material to allow for tissue ingrowth.

6. The implant of claim 1, wherein at least one of the plurality of attachment pegs is provided with a porous coating to allow for tissue ingrowth.

7. The implant of claim 1, further comprising a thin impermeable membrane extending about a side wall of at least one of the plurality of attachment pegs to prevent boney tissue ingrowth into the side wall while allowing boney tissue ingrowth into a bottom wall of the at least one attachment peg.

8. The implant of claim 1, wherein the base portion is provided with a plurality of indentations positioned about its periphery to allow for the polymeric material of the polymeric portion to flow about the periphery to bond the polymeric portion to the base portion.

9. The implant of claim 1, wherein the polymeric portion extends about sides of the base portion.

10. The implant of claim 1, wherein the porous metallic material is selected from the group consisting of titanium, titanium alloy, zirconium, chrome cobalt, and stainless steel.

11. The implant of claim 1, wherein the polymeric material comprises a polyethylene material or a cross-linked polyethylene material.

12. The implant of claim 1, wherein the polymeric portion encapsulates the top surface of the base portion.

13. The implant of claim 1, wherein the patellar implant is sized and configured for implantation into a patient's natural patella adjacent a femoral implant, and wherein the polymeric portion is adapted to bear against the femoral implant.

14. A patellar implant, comprising:
a base portion comprising a porous metallic material and having a porous top surface and a porous bottom surface, the porous top surface comprising an annular ring extending therefrom, wherein the annular ring comprises a toroidal shape with inner and outer surfaces and a portion of the inner surface overhangs an inner portion of the porous top surface and a portion of the outer surface overhangs an outer portion of the porous top surface; and
a polymeric portion comprising a polymeric material, the polymeric portion attached to the base portion about at least part of the inner and outer surfaces of the annular ring and such that the polymeric material bonds with the porous top surface and encapsulates the porous top surface of the base portion, wherein the polymeric portion attached to the base portion fills at least a portion of the overhang between the portion of the inner surface of the toroidal shape and the inner portion of the porous top surface of the base portion and the polymeric portion attached to the base portion fills at least a portion of the overhang between the portion of the outer surface of the toroidal shape and the outer portion of the porous top surface of the base portion.

15. The implant of claim 14, comprising a membrane embedded below the top porous surface.

16. The implant of claim 15, wherein the membrane is embedded in the porous metallic material of the base portion.

17. The implant of claim 14, further comprising:
at least one attachment peg extending from the porous bottom surface of the base portion and formed of the porous metallic material; and
a thin impermeable membrane extending about a side wall of the at least one attachment peg to prevent boney tissue ingrowth into the side wall while allowing boney tissue ingrowth into a bottom wall of the at least one attachment peg.

18. The implant of claim 14, wherein the polymeric portion extends about sides of the base portion.

19. The implant of claim 14, wherein the porous metallic material is selected from the group consisting of titanium, titanium alloy, zirconium, chrome cobalt, and stainless steel.

20. The implant of claim 14, wherein the patellar implant is sized and configured for implantation into a patient's natural patella adjacent a femoral implant, and wherein the polymeric portion is adapted to bear against the femoral implant.

* * * * *